United States Patent
Jobst et al.

(10) Patent No.: US 9,429,665 B2
(45) Date of Patent: Aug. 30, 2016

(54) RADIATION PENETRATION SYSTEM AND CALIBRATION OF THE SAME

(71) Applicant: FRAUNHOFER-GESELLSCHAFT ZUR FOERDERUNG DER ANGEWANDTEN FORSCHUNG E.V., Munich (DE)

(72) Inventors: Andreas Jobst, Nuremberg (DE); Guenther Kostka, Erlangen (DE); Peter Schmitt, Erlangen (DE)

(73) Assignee: Fraunhofer-Gesellschaft zur Foerderung der angewandten Forschung e.V., Munich (DE)

(*) Notice: Subject to any disclaimer, the term of this patent is extended or adjusted under 35 U.S.C. 154(b) by 252 days.

(21) Appl. No.: 14/076,138

(22) Filed: Nov. 8, 2013

(65) Prior Publication Data

US 2014/0064458 A1    Mar. 6, 2014

Related U.S. Application Data

(63) Continuation of application No. PCT/EP2012/058495, filed on May 9, 2012.

(30) Foreign Application Priority Data

May 9, 2011 (DE) .................. 10 2011 075 527

(51) Int. Cl.
*G01T 7/00* (2006.01)
*A61B 6/00* (2006.01)
*A61B 6/02* (2006.01)
*A61B 6/03* (2006.01)

(52) U.S. Cl.
CPC .............. *G01T 7/005* (2013.01); *A61B 6/00* (2013.01); *A61B 6/027* (2013.01); *A61B 6/583* (2013.01); *A61B 6/585* (2013.01); *A61B 6/03* (2013.01); *A61B 6/4429* (2013.01)

(58) Field of Classification Search
CPC ....... A61B 6/583; A61B 6/585; A61B 6/582; A61B 6/4233; A61B 6/4021
See application file for complete search history.

(56) References Cited

U.S. PATENT DOCUMENTS

| 5,748,768 | A  | 5/1998  | Sivers et al.  |
|-----------|----|---------|----------------|
| 6,236,704 | B1 | 5/2001  | Navab et al.   |
| 6,471,399 | B1 | 10/2002 | Zylka et al.   |
| 7,591,589 | B2 | 9/2009  | Grebner et al. |

(Continued)

FOREIGN PATENT DOCUMENTS

| DE | 10030633 A1 | 1/2001 |
|----|-------------|--------|
| DE | 10301941 A1 | 8/2004 |

(Continued)

*Primary Examiner* — Hoon Song
(74) *Attorney, Agent, or Firm* — Michael A. Glenn; Perkins Coie LLP

(57) ABSTRACT

Position errors of the flat-panel detector in the axes system of the radiation penetration system relative to a necessitated position which remain, for example, after a coarse setup of the radiation penetration system are balanced and thus the accuracy of the radiation penetration system is brought almost randomly close to the accuracy which would have resulted if the flat-panel detector had been exactly adjusted mechanically subsequently by executing a geometrical correction of the radiation penetration raw image, so that a change of a projection of the penetrated object in the radiation penetration raw image due to the position error is reduced or corrected.

24 Claims, 9 Drawing Sheets

(56) References Cited

U.S. PATENT DOCUMENTS

| | | |
|---|---|---|
| 7,706,634 B2 | 4/2010 | Schmitt et al. |
| 2003/0207749 A1 | 11/2003 | Bauer et al. |
| 2005/0117708 A1* | 6/2005 | Cho ............... A61B 6/547 378/164 |
| 2007/0041508 A1 | 2/2007 | Tubbs |
| 2011/0228906 A1* | 9/2011 | Jaffray ............ A61B 6/032 378/65 |
| 2013/0315372 A1* | 11/2013 | Behiels ............ A61B 6/06 378/62 |

FOREIGN PATENT DOCUMENTS

| | | |
|---|---|---|
| DE | 102007021770 A1 | 11/2008 |
| EP | 1078599 A1 | 2/2001 |
| WO | 2004/066612 A1 | 8/2004 |
| WO | 2008/054717 A2 | 5/2008 |

* cited by examiner

RADIATION PENETRATION SYSTEM AND CALIBRATION OF THE SAME

CROSS-REFERENCE TO RELATED APPLICATIONS

This application is a continuation of copending International Application No. PCT/EP2012/058495, filed May 9, 2012, which is incorporated herein by reference in its entirety, and additionally claims priority from German Patent Application No. 102011075527.6, filed May 9, 2011, which is also incorporated herein by reference in its entirety.

BACKGROUND OF THE INVENTION

The present invention relates to a radiation penetration system, such as, e.g., computer tomographs or the like, and a calibration of such systems.

Radiation penetration systems frequently operate using X-radiation. Flat-panel detectors of radiation penetration systems frequently have a screen, like, e.g., a scintillator screen for X-ray-sensitive flat-panel detectors, which is then recorded using one or several optical cameras. In this way, for example, X-ray cameras exists which are used, for example, in digital radioscopy or computer tomography for quality control of products or for metrology.

Due to their setup, conventional imaging X-ray flat-panel cameras, such as, e.g., flat screen detectors on the basis of amorphous silicon, generally comprise square pixels which fill the active detector surface more or less completely, i.e. completely sample the scintillator surface. The alignment of the lines and columns and their spacing are predetermined depending on the design in these X-ray cameras and cannot be changed. An exception is the so-called binning, i.e. combining several neighboring pixels into one image point, wherein the resolution and the amount of data may be reduced and the signal-to-noise ratio may be improved.

For certain applications of these X-ray cameras, it is necessitated to adjust the camera in a mechanically exact way in an assembly such that the lines and columns have a defined orientation with respect to other components of the assembly, for example the mechanical positioning axes. With decreasing pixel size or increasing resolution of the camera, also requirements on the accuracy and stability of mechanical adjustment between the camera and the other assembly components increase, such as, e.g., the manipulator, which includes, for example, a robot arm, a C-frame or the like.

The adjustment of radiation penetration systems has up to now been cost- and time-consuming for this reason and has included an iterative and approximative process in which radiation penetrations were executed alternatingly on calibration objects and the thus acquired measurements were used for readjusting the flat-panel detector.

It is the object of the present invention to provide a radiation penetration system and a method and a device for calibrating the same so that an improved tradeoff between adjustment on the one hand and measurement accuracy on the other hand may be acquired, i.e., for example, the same measurement accuracy with less adjustment effort, and this, in turn, with little additional hardware and/or software expenditure.

SUMMARY

According to an embodiment, a method for calibrating a radiation penetration system having a radiation source, a flat-panel detector for generating radiation penetration raw images of an object, a manipulator which is implemented to change a relative position between the radiation source, the object and the flat-panel detector, wherein the axes system is defined by at least one movement axis of the manipulator and one beam axis between the radiation source and the flat-panel detector, and a preprocessor for applying correction data to the radiation penetration raw images of the object to acquire radiation penetration images of the object, may have the steps of: generating radiation penetration raw images of a calibration object in different relative positions changed with respect to each other by the manipulator between the radiation source, the calibration object and the flat-panel detector on the basis of radiation which penetrates the calibration object between the radiation source and the flat-panel detector, by the flat-panel detector; and readjusting the correction data depending on the radiation penetration raw images of the calibration object so that the application of the readjusted correction data leads to a geometrical correction of the radiation penetration raw images, so that a change of a projection of the object in the radiation penetration raw image due to a position error of the flat-panel detector in the axes system relative to a necessitated position is reduced, wherein the position error of the flat-panel detector is defined as a tilting of a column or line direction of the flat-panel detector relative to a rotation or translation positioning axis of the manipulator, or a tilting of the column or line direction of the flat-panel detector relative to a trajectory along which the flat-panel detector moves relative to the object between the plurality of radiation penetration raw images.

According to another embodiment, a device for calibrating a radiation penetration system having a radiation source, a flat-panel detector for generating radiation penetration raw images of an object, a manipulator which is implemented to change a relative position between the radiation source, the object and the flat-panel detector, wherein the axes system is defined by at least one movement axis of the manipulator and a beam axis between the radiation source and the flat-panel detector, and a preprocessor for applying correction data to the radiation penetration raw images of the object to acquire radiation penetration images of the object, may have: a means for generating radiation penetration raw images of a calibration object in different relative positions changed with respect to each other by the manipulator between the radiation source, the calibration object and the flat-panel detector on the basis of radiation which penetrates the calibration object between the radiation source and the flat-panel detector, by the flat-panel detector; and a means for readjusting the correction data depending on the radiation penetration raw images of the calibration object so that the application of the readjusted correction data leads to a geometrical correction of the radiation penetration raw images, so that a change of a projection of the object in the radiation penetration raw image due to a position error of the flat-panel detector in the axes system relative to a necessitated position is reduced, wherein the position error of the flat-panel detector is defined as a tilting of a column or line direction of the flat-panel detector relative to a rotation or translation positioning axis of the manipulator, or a tilting of the column or line direction of the flat-panel detector relative to a trajectory along which the flat-panel detector moves relative to the object between the plurality of radiation penetration raw images.

Another embodiment may have a radiation penetration system having the above device for calibrating the radiation penetration system.

Another embodiment may have a computer program having a program code for executing the above method for calibrating a radiation penetration system when the program is executed on a computer.

It is a finding of the present invention to have recognized that it is possible to balance position errors of the flat-panel detector in the system of coordinates (or system of axes) of the radiation penetration system with respect to a necessitated position which, for example, remain after a coarse setup of the radiation penetration system and to thus bring the accuracy of the radiation penetration system almost arbitrarily close to the accuracy which would have resulted if the flat-panel detector had been subsequently adjusted in a mechanically exact manner when a geometrical correction of the radiation penetration raw image is executed, so that a change or an error, such as, e.g., a distortion, a displacement and a deviation in size or the like, of a projection of the radiation-penetrated object in the radiation penetration raw image due to the position error is reduced or corrected.

According to embodiments, the finding is exploited that radiation penetration systems frequently already use flat-panel detectors which are able to generate radiation penetration raw images having a higher resolution than the radiation penetration images which are actually to be utilized after preprocessing. It is thus possible to balance position errors of the flat-panel detector in the axes system of the radiation penetration system relative to a necessitated position even better which remain, for example, after a rough or coarse setup of the radiation penetration system or to bring the accuracy of the radiation penetration system almost arbitrarily close to the accuracy which would have resulted if the flat-panel detector had subsequently been adjusted in a mechanically exact manner, i.e. by executing a geometrical correction of the radiation penetration raw image in a resolution which is higher than a resolution of the finally necessitated radiation penetration image, so that a change of a projection of the radiation-penetrated object in the radiation penetration raw image due to the position error is reduced or corrected.

According to one embodiment, the radiation penetration system may comprise a reconstructor which is implemented to reconstruct the object from radiation penetration images which have been acquired from a plurality of radiation penetration raw images by preprocessing. In this case, there are several possibilities for the necessitated position of the flat-panel detector relative to the axes system of the radiation penetration system. The axes system may be defined by the beam or ray axis between the radiation source and the flat-panel detector, a rotation axis of the manipulator, a translation positioning axis of the manipulator, a trajectory of the flat-panel detector between the generation of the radiation penetration raw images which are later used for reconstruction, i.e. by all these axes, a part of the same or only one of these axes, and the necessitated position may provide for the flat-panel detector to be perpendicular to these axes or for a column or line direction of the flat-panel detector to be aligned in parallel to one of these axes or for the radiation penetration images which, for example, comprise a regular pixel array arrangement of lines and columns to be aligned with their line and/or column directions in parallel with a respective axis of the axes system, or for a certain angle to be maintained.

According to one embodiment, the flat-panel detector comprises a plurality of flat-panel detector arrays for generating partial images which, by mutually overlapping, together respectively result in a radiation penetration raw image. In this case, the geometrical correction may be executed together with combining or stitching of the partial images and/or a simultaneous equalization of the partial images. In a calibration of the radiation penetration system, for example the correction data underlying the preprocessing may initially be pre-calibrated to execute the stitching and, if applicable, the partial image-individual equalization, while a modification of the calibration data is again executed after the setup of the radiation penetration system to equalize possible position errors of the flat-panel detector and thus reduce the mechanical effort of calibration or assembly or setup of the radiation penetration system.

According to a further embodiment, the above findings are utilized by giving a radiation penetration system with an equiangular pixel arrangement a simple possibility of adjusting the detector/source distance by executing the above geometrical correction, depending on the set distance, in order to acquire an equiangular radiation penetration image. The correction data may be determined in a similar way, so that the same possibly simultaneously execute corrections other than only a transition, for example, from an arrangement of the pixels of the flat-panel detector in columns and lines to the equiangular pixel arrangement, such as, e.g., a balancing of tilt or the like.

BRIEF DESCRIPTION OF THE DRAWINGS

In the following, embodiments of the present invention will be explained in more detail with reference to the accompanying drawings, in which.

DETAILED DESCRIPTION OF THE INVENTION

Figure 1:
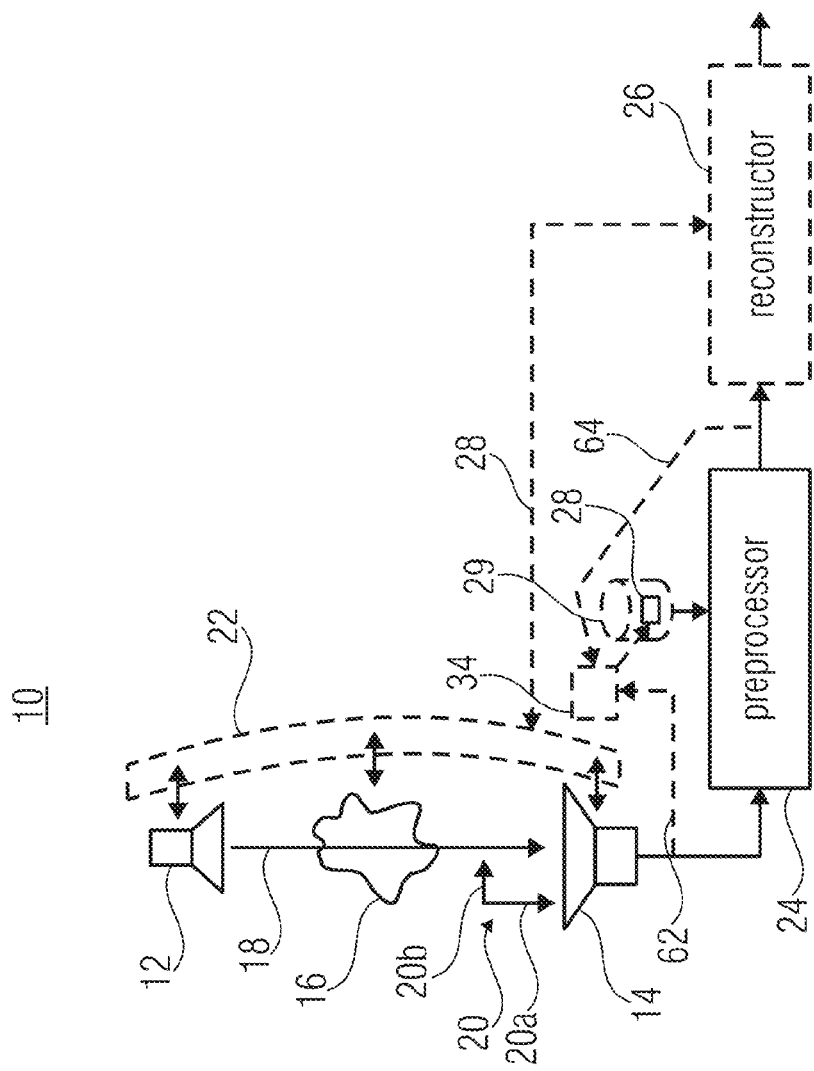
FIG. 1 is a schematical block diagram of a radiation penetration system according to one embodiment.

FIG. 1 shows a radiation penetration system 10 according to one embodiment of the present application. The radiation penetration system of FIG. 1 includes a radiation source 12, such as, e.g., an X-ray source, and a flat-panel detector 14 for generating a radiation penetration raw image of an object 16 on the basis of radiation 18, such as, e.g., X-radiation which penetrates the object 16 between the radiation source 12 and the flat-panel detector 14. As will be described later with reference to FIG. 3, the flat-panel detector 14 may, for example, comprise a scintillator screen which converts the radiation 18 in a spatially resolved way into optical information, wherein the screen is again recorded by one or several optical cameras, if applicable via one or several mirrors for protecting the cameras from the radiation 18. An image plane may be allocated to the flat-panel detector 14 and comprises within this image plane a distribution of pixels or pixel positions. The scintillator screen of the flat-panel detector 14 forms, for example, this image plane, wherein the pixel positions in the image planes are defined by the distribution of the pixels of the optical cameras in their object plane defined by the camera objective, i.e. the scintillator screen.

The radiation penetration system 10 is constructed such that an axes system is determined by the same. The axes system is exemplarily indicated in FIG. 1 by reference numeral 20. As may be gathered from the following description, the axes system may, for example, comprise a beam axis 20a along which the for example parallelized radiation 18 impinges upon the flat-panel detector 14, or a motion axis 20b of an optional manipulator 22 of the radiation penetration system 10 which can be implemented to change a relative position between the radiation source 12, the object 16 and the flat-panel detector 14.

The radiation penetration system 10 further includes a preprocessor 24 for preprocessing the radiation penetration raw image into a radiation penetration image which has a resolution which is lower than a resolution of the radiation penetration raw image as was generated by the flat-panel detector 14. In particular, the preprocessor 14 executes the preprocessing of the radiation penetration raw image into the radiation penetration image by a geometrical correction of the radiation penetration raw image in a resolution which is higher than a resolution of the radiation penetration image, so that a change of a projection of the object in the radiation penetration raw image due to a position error of the flat-panel detector 14 in the axes system 20 is reduced with respect to a necessitated position. This more or less means the following: the flat-panel detector 14 comprises, for example, a radiation-sensitive surface A in the image plane, i.e. sampled in N pixels in the image plane. The quotient N/A may be regarded as a measure for the resolution of the radiation penetration raw images generated by the flat-panel detector 14. The radiation penetration system 10 subsequently utilizes radiation penetration images which have a lower resolution, i.e. a resolution wherein the radiation-sensitive area A of the flat-panel detector 14 is sampled with less pixels n<N. As will be explained in the following, the distribution of the pixels of both the radiation penetration raw images and the radiation penetration images may be a regular distribution of the pixels in columns and lines, wherein the distribution in the radiation penetration images may be regular, i.e., for example, Cartesian or affine, whereas the distribution in the radiation penetration raw images may comprise an irregularity, as is later described exemplarily with reference to FIG. 3.

Figure 6:
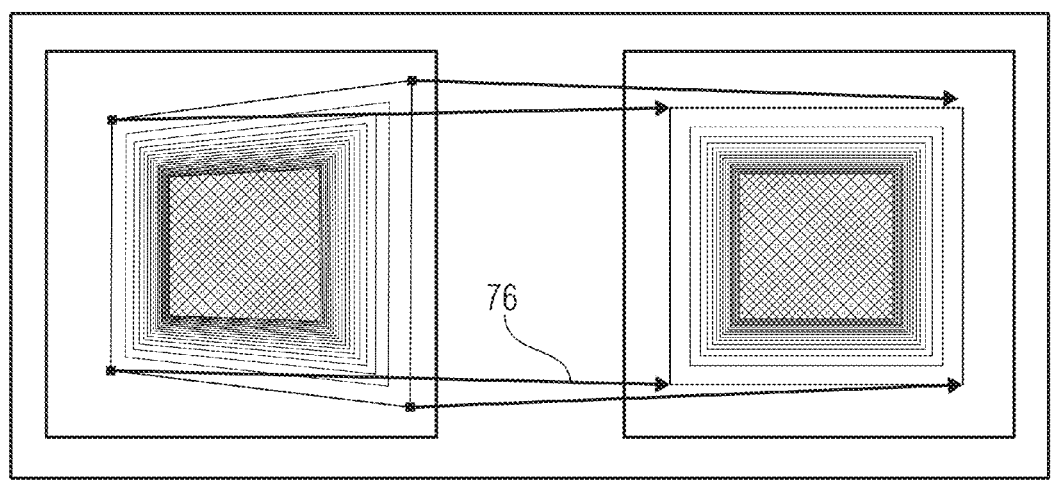
FIG. 6 on the left is a radiation penetration image with a tilted flat-panel detector without a geometrical correction and on the right is the radiation penetration image with a correctly arranged flat-panel detector.

The radiation penetration system 10 is provided, however, to generate radiation penetration images which represent a projection of the object 16 onto an image plane of the flat-panel detector 14 in a state in which the same is in a certain necessitated position, such as, e.g., perpendicular to the above-mentioned beam axis 20a or in a different exemplary necessitated position with respect to the axes system 20. If the image plane of the flat-panel detector 14 is tilted with respect to this necessitated position, the projection of the object 16 onto the image plane appears distorted, an example of which is illustrated in FIG. 6, and if the image plane is arranged at a wrong position along one of the axes, i.e., for example, too far from the radiation source 12, or if it is twisted with respect to one of the axes, the projection of the object 16 may, for example, appear centrally stretched or shrunk or twisted in the radiation penetration raw images, which may have disadvantages in the subsequent utilization of the radiation penetration images, such as, e.g., a reconstructor 26 of the radiation penetration system 10, which is, for example, implemented to reconstruct the object from a plurality of radiation penetration images which have been acquired by the preprocessor 24 from radiation penetration raw images generated by the flat-panel detector 14 by changing the relative position between the radiation source 12, the object 16 and the flat-panel detector 14 between the radiation penetration raw images, and which takes the necessitated position of the detector 14 as a basis. The reconstructor 26 reconstructs, for example on the basis of the radiation penetration images and from information on the relative position between the radiation source 12, the object 16 and the flat-panel detector 14, in which the same were generated by radiation images or the radiation penetration raw images underlying the same, a spatial distribution, for example of the density of the object, a distribution of the occurrence of a certain material or a distribution of the density or the occurrence of a certain atomic number in the object, i.e. more generally, a spatial distribution of material characteristics of the object.

The radiation penetration system 10 of FIG. 1 now compensates an erroneous adjustment or the position error of the flat-panel detector 14 with respect to the above-described necessitated position by executing the geometrical correction of the radiation penetration raw image by the flat-panel detector 14 in a resolution which is higher than the resolution of the respective radiation penetration image which results from the preprocessing in the preprocessor 24. In other words, the above-mentioned distortion, centric stretching or twisting or rotation of the object in the image plane is transformatively taken into consideration in a resolution in preprocessing which is higher than the final resolution of the radiation penetration images which are finally utilized, such as, e.g., by the optional reconstructor 26.

Before a method of calibrating the radiation penetration system 10 of FIG. 1 is described with reference to FIG. 2, it is to be noted that the optional manipulator 22 may, for example, be a C-frame, onto which the radiation source 12 and the flat-panel detector 14 are mounted facing each other across an axis of rotation around which again the C-frame may be pivoted to be able to X-ray the, for example, fixed object 16 from different directions. The manipulator 22 may, for example, also be a robot arm or two robot arms, one for the radiation source 12 and the other for the flat-panel detector 14, or the manipulator 22 additionally or alternatively comprises a translation positioning path or the like. The radiation 18 emitted by the radiation source 12 may be parallelized or divergently fanned out. As is illustrated by a dashed arrow 28, it may be the case that the optional reconstructor 26 is coupled to the manipulator 22 to know, with respect to each radiation penetration image, in which relative position the radiation source 12, the object 16 and the flat-panel detector 14 were located when the respective radiation penetration raw image was generated with respect to the respective radiation penetration image. The reconstructor 26 then reconstructs the object 16 from the plurality of radiation penetration images in different relative positions, i.e. reconstructs its spatial density distribution or the like. However, also other possibilities for an implementation of the radiation penetration system 10 exist, and examples are provided in the following.

It is finally to be noted that the preprocessor 24 may be implemented in a hard-wired form, in a programmable logic or in software, wherein the same applies to the reconstructor 26. A computer may, for example, take over the operations of the preprocessor 24 and the reconstructor 26. The preprocessor 24 may, however, also be positioned for example in a housing of the flat-panel detector 14 or between the reconstructor 26 and the flat-panel detector 14.

Figure 2:
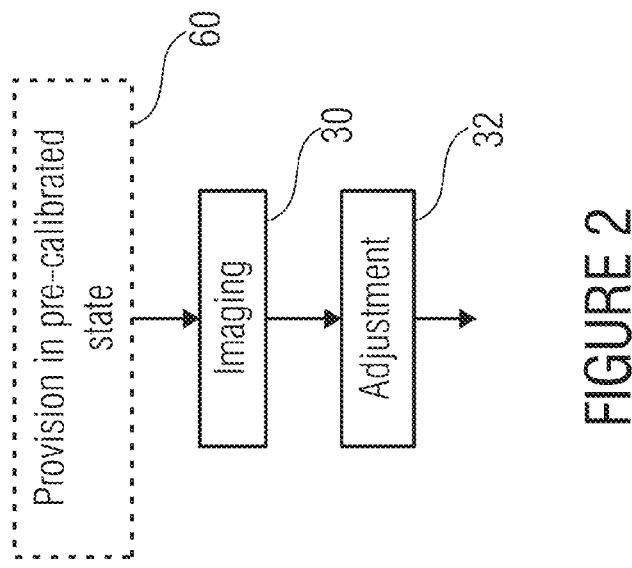
FIG. 2 is a flowchart of a method for calibrating a radiation penetration system according to FIG. 1.

FIG. 2 now shows a method of procedure for calibrating the radiation penetration system 10 of FIG. 1 according to one embodiment. It is assumed here that the preprocessor 24 executes preprocessing by accessing certain correction data 28 or by applying these correction data 28 to the radiation penetration raw images of the flat-panel detector 14. As is indicated in FIG. 1, the correction data 28 may, for example, be located in a memory 29, which the preprocessor 24 accesses to acquire the correction data 28 depending on which the preprocessor 24 then executes the preprocessing. The memory 29 may, for example, be a non-volatile memory, such as, e.g., a write-once read-only memory. It is, however, to be noted that the correction data 28 may also be integrated in a possible software implementation of the preprocessor 24, i.e. in the program code itself.

The method of FIG. 2 starts by generating at least one radiation penetration raw image of a calibration object 16 by the flat-panel detector 14. As will be described later with reference to FIG. 7, the calibration object may, for example, be a sphere or a ball of material strongly absorbing the radiation 18, and it may be the case that several radiation penetration raw images of this calibration object are recorded, wherein between the same the manipulator 22 changes the relative position between the radiation source 12, the calibration object and the flat-panel detector 14, such as, e.g., in the case of a fixed opposing position of the radiation source 12 with respect to the flat-panel detector 14. The manipulator 22 rotates the latter pair for example round an axis of rotation which is only so distant from the ball that in every rotary position of the radiation source/flat-panel detector pair with respect to the axis of rotation the calibration object is projected completely onto the area-sensitive area of the flat-panel detector 14 or is contained in the radiation penetration raw images.

After this step 30 designated in FIG. 2 as imaging, a step 32 of setting the correction data 28 of the preprocessor follows, depending on the at least one radiation penetration raw image of step 30, so that the application of the set correction data 28 leads to a geometrical correction of radiation penetration raw images of the flat-panel detector 14, i.e. in a resolution which is higher than the resolution of the radiation penetration images and so that the above-mentioned change in the projection of objects is acquired in the radiation penetration raw images. Here, the step of setting 32 may, for example, include the initial storage of the correction data 28 into the memory or overwriting already existing (pre-calibrated) correction data with the new correction data. The step of setting 32 may, for example, comprise computing or calculating the correction data 28 using a parameterized computing specification or looking up a table. The step 32 may further include extracting designated points, such as, e.g., a center point of the calibration object in the one or several radiation penetration raw images of step 30 or the determination of their position within the same to determine the new correction data for the setting in step 32 from these positions.

The system 10 of FIG. 1 may include a device for executing the method of FIG. 2. It is designated by 34 in FIG. 1. It is connected to the memory 29 and, as mentioned above, receives the raw images, for example, directly at the output of the detector 14 or uses images pre-calibrated by the preset correction data 28 at the output of the detector 14 for the setting in step 32.

After the basic setup and the functioning of the radiation penetration system of FIG. 1 and its calibration have been described above, in the following, with reference to detailed embodiments for the individual components possible details of implementation are to be presented which improve understanding.

Thus, the above-described position error of the flat-panel detector 14 in the axes system 20 relative to the necessitated position may, for example, be a tilting of the flat-panel detector 14 or an image plane of the same from a perpendicular alignment to a beam axis 20a between the radiation source 12 and the flat-panel detector 14. The beam axis 20a is defined in the case of a parallelization of the beam 18 by the direction of the beam 18 as it was emitted from the radiation source 12. In the case of divergent radiation beam or bundle 18 output from the radiation source 12, the beam axis 20a may also be defined along the respective beam 18 which passes perpendicularly for example through an axis of rotation of the manipulator 22, or perpendicular to a translational plane of the manipulator 22, around which or along which the manipulator 22 moves the pair consisting of the radiation source 12 and the flat-panel detector 14, for example as the manipulator 22 is mechanically constructed such that this axis of rotation or this translational plane is specified constructively or given by a trajectory, along which the radiation source 12 and the flat-panel detector 14 are to move during the generation of radiation penetration raw images which are then used for a possible reconstruction by the reconstructor 26.

Additionally or alternatively, the above-mentioned position error of the flat-panel detector 14 may be a tilting of a column or line direction of the flat-panel detector 14 relative to a rotational or translational positioning axis of the manipulator 22, i.e. a deviation from a parallel alignment with respect to the same. If the flat-panel detector 14 does not comprise any irregularity regarding the arrangement of the pixel position in the image plane, the mentioned column and line direction corresponds to the pixel positions of the flat-panel detector 4 in the image plane arranged along these directions. In the case of the example of a distribution of the pixel positions in the image plane which is described later with reference to FIG. 3, the mentioned column or line direction corresponds, for example, to an averaged column or line direction of the actual pixel positions of the flat-panel detector 14 in the image plane or projection plane or to a distribution of the pixel positions of the flat-panel detector 14 of the image plane in a pre-calibration state, as is described in the following with reference to FIGS. 3 and 4. The above-mentioned translational positioning axis may, for example, be the translational axis along which the manipulator 22 moves the radiation source 12 and the flat-panel detector 14 in a helical trajectory.

The above-mentioned position error of the flat-panel detector may also be a tilting in the above-mentioned column or line direction of the flat-panel detector 14 with respect to a trajectory along which the flat-panel detector 14 moves relative to the object 16 between the plurality of radiation penetration raw images or their generation. The trajectory may, for example, be the above-mentioned helical track.

Figure 3:
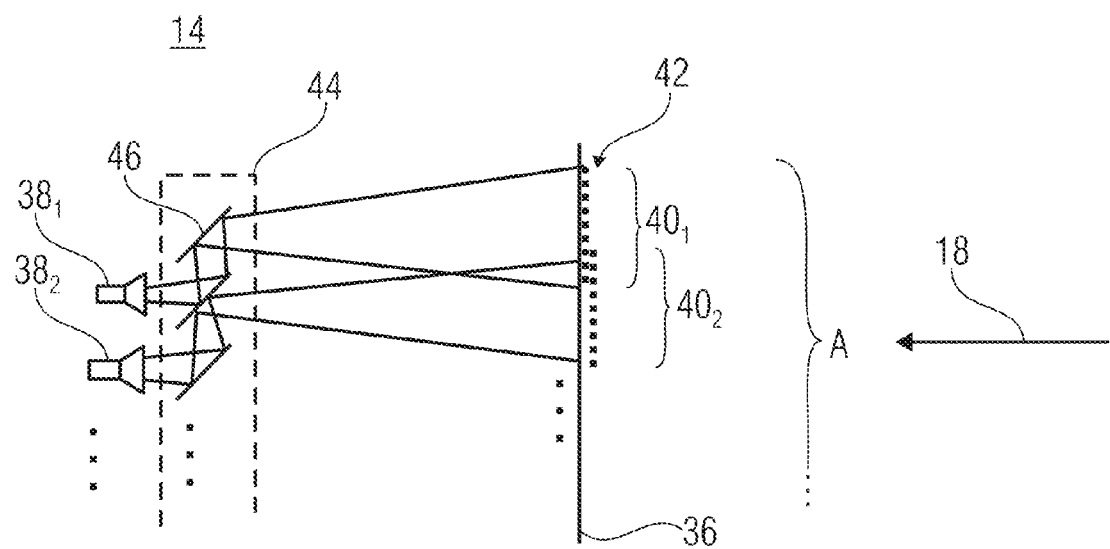
FIG. 3 is a schematical sectional side view of a flat-panel detector according to one embodiment.

Before, in the following, further possible details are presented as to how the individual components of the radiation penetration system 10 of FIG. 1 are set up and cooperate, such as, e.g., within the scope of a radiation penetration reconstruction system, in the following with reference to FIGS. 3 and 4 an example is given of the fact that the flat-panel detector 14 may possibly comprises an irregularity with respect to the distribution of the pixel positions in the image plane. FIG. 3 shows such an example of a flat-panel detector 14. The flat-panel detector 14 of FIG. 3 includes a scintillator screen 36 and several cameras $38_1$ and $38_2$. The cameras $38_1$ and $38_2$ are set such that their focal depth plane or their focal depth area coincides with the scintillator plane of the scintillator screen 36 and such that the image sections $40_1$ and $40_2$ recorded by the individual cameras $38_1$ and $38_2$ completely cover the above-mentioned radiation-sensitive area A of the scintillator screen. It is of advantage here, as is illustrated in FIG. 3, for the sections $40_1$ and $40_2$ of neighboring cameras $38_1$ and $38_2$ to mutually overlap. The images of the pixels of the pixel arrays (not shown) of the cameras $38_1$ and $38_2$ which are located across the objectives (not shown) of this camera in the object plane of the same, which again may coincide with the scintillator screen 36, define, in the case of the camera of FIG. 3, the above-mentioned distribution 42 of pixel positions in the image plane of the camera 14.

Due to the overlap and due to positioning inaccuracies between the cameras $38_1$ and $38_2$, the distribution 42 comprises irregularities with respect to a regular distribution in columns and lines, for example, corresponding to the distribution of the pixels in the pixel arrays of the cameras $38_1$ and $38_2$.

The camera 14 is built into the radiation penetration system 10 such that the radiation 18 impinges upon the scintillator screen 36, i.e., for example, essentially perpendicularly, as has been described above, and that there the radiation is converted into an optical information distribution where the same is locally sampled by the cameras $38_1$ and $38_2$ with the distribution of the pixels.

As is exemplarily illustrated at 44, the flat-panel camera 14 may include a mirror array of mirrors 46, via which the cameras $38_1$ and $38_2$ image or map the scintillator screen 36 by means of mirrorings at the mirrors 46 to their respective pixel array to be thus, if applicable, protected, for example, against the higher-energy radiation 18.

Figure 4:
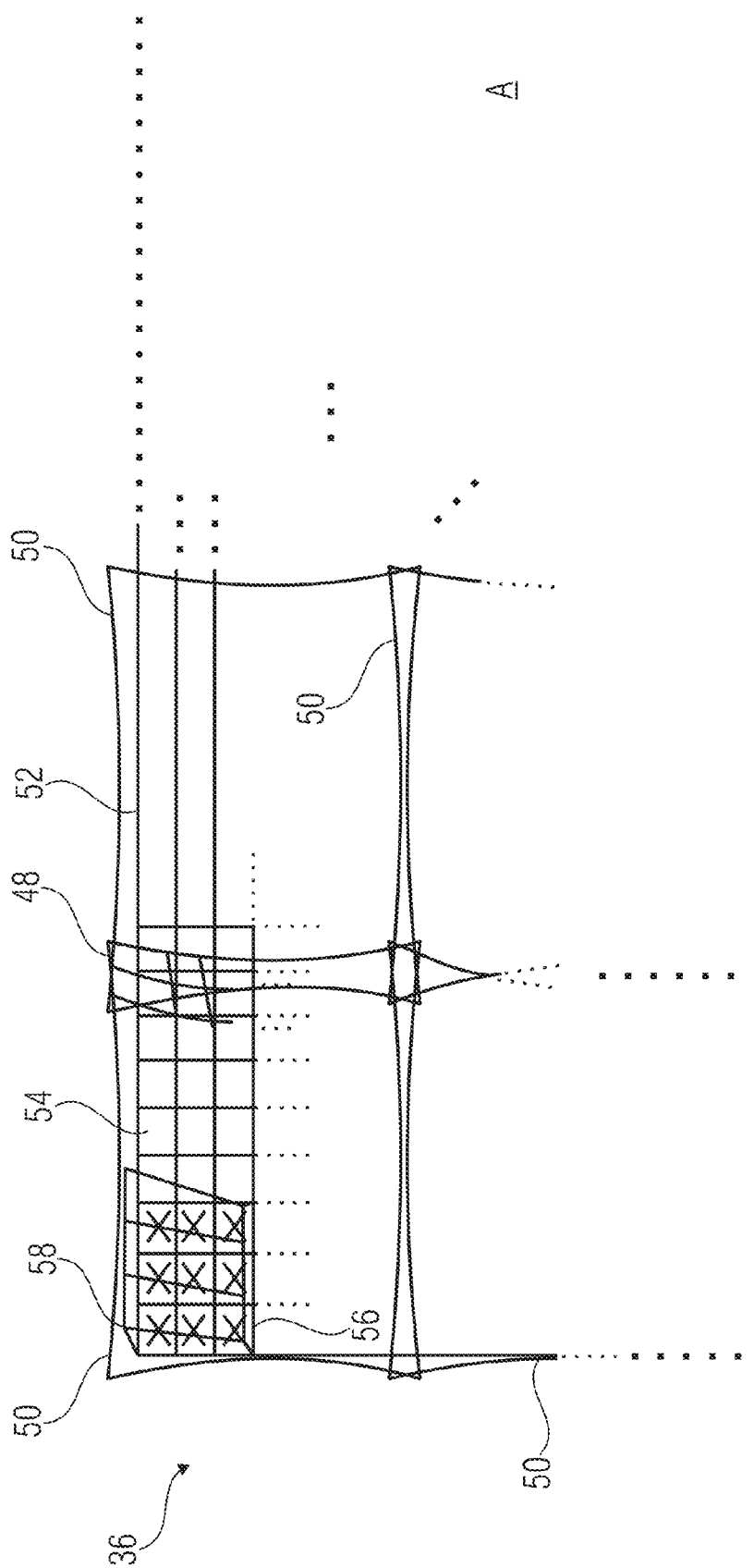
FIG. 4 is a schematical sectional view of the distribution of pixels or pixel detector positions in an image plane of the flat-panel detector of FIG. 3 according to one exemplary embodiment.

With reference to FIG. 4, using the example of FIG. 3, the connection between the irregular distribution 42 of pixels, the radiation penetration raw images and the radiation penetration images is to be described. FIG. 4 shows the pixel distributions in the image plane or the projection plane of the flat-panel camera 14, i.e. for example in the plane of the scintillator screen 36. As mentioned above, in the radiation-sensitive area part A the pixel positions 48 of the flat-panel camera 14 are distributed, i.e. in the case of FIG. 3 the images of the pixels of the pixel arrays of the cameras $38_1$ and $38_2$. As is indicated by pulvinated rectangles 50, the visual field of each individual camera with its pixels 48 for example covers a region 50 which laterally overlaps the regions 50 of neighboring cameras, such as, for example, 0.1% to 3% of the number of pixels of the respective camera in the respective direction of overlap. As is indicated in FIG. 4, also the partial regions 50 may be arranged regularly in columns and lines.

As already mentioned above, the distribution of the pixels 48 in the image plane of the camera 14 deviates from a purely regular distribution in columns and lines due to distortions by the objectives of the cameras $38_1$ and $38_2$, due to tilting and twisting or rotating of the cameras and/or due to mutual position inaccuracies of the cameras $38_1$ and $38_2$ in parallel to the image plane 36. For better understanding, the distortions in FIG. 4 are slightly exaggerated. Also the relation of the size of the pixels with respect to the partial regions 50 was illustrated in an enlarged way for better understanding.

If recordings are now made using the flat-panel camera 14 of FIGS. 3 and 4, the partial images 50 of the individual cameras may not be simply combined in order to acquire a sensible image. The partial images have, rather, to be aligned with each other or be combined, which is also referred to as stitching. Simultaneously, the distortions may be corrected etc. until, by a corresponding interpolation from the original pixel values of the pixels 48, a sample of the radiation-sensitive surface portion A in a pixel grid 52 results, for example comprising regularly distributed pixels 54 in columns and lines, as is indicated in FIG. 4. The resolution of the pixel grid 52 may, for example, be the same as or slightly smaller than the resolution of the distribution 42 of the pixels 48 and, for example, be larger than the final resolution of the radiation penetration images.

In order to acquire the sample in the pixel grid 52, it is, for example, defined in correction data for each pixel 54 of the pixel grid 52 how adjacent pixels 48, for example overlapping with the respective pixel 54, are to be combined or added in a weighted manner to each other in order to result in the respective pixel value of the respective pixel 54.

The last-mentioned transition from the irregular distribution 42 to the regular distribution 52 may exemplarily already be executed upstream from the preprocessor 24, for example already in the flat-panel camera 14. In the following, embodiments are described, wherein this processing is executed in the preprocessor 24 itself, wherein the correction data are then modified in order to also execute the geometrical correction as it results, in order to balance the possible position errors of the flat-panel detector 14 in the radiation penetration system 10. If, however, the transition to the regular distribution 52 has already been executed before the preprocessor 24, then, for example, this distribution 52 of the pixels 54 concerns the radiation penetration raw images which enter the preprocessor 24 from the flat-panel camera. The resolution of the radiation penetration raw images, as mentioned above, is, however, higher than that of the radiation penetration images finally to be output by the preprocessor, i.e., for example, to an optional reconstructor 26. If the flat-panel detector 14 were correctly built into the coordinate system or axes system 20 at its necessitated position, the preprocessor 24 would only have to execute a binning, i.e. a combination of neighboring pixels 54 of the regular pixel grid 52, in order to execute a resolution reduction in this manner, wherein this binning is exemplarily indicated in FIG. 4 by a 3-3 binning, so that 3×3 blocks each of pixels 53 would result in a pixel 56 of a radiation penetration image at the output of the preprocessor 24. Due to the position error of the flat-panel detector 14, however, the projection of the object 16 into the plane 36 is changed geometrically, i.e., for example, distorted, centrally stretched or the like, and the above-mentioned correction data 28 are thus to be provided to again correct the geometrical change at the transition into the lower resolution of the radiation penetration images, but not only in the resolution of the radiation penetration images with the pixels 56, but in a higher resolution, such as, e.g., already in the resolution of the pixel grid 52. For example, the device 34 determines in step 32 that the pixels 54 which together result in the larger pixel 56, would have to be shifted in the image plane 36 as indicated at 58, in order to result in a sample of the radiation penetration 18, which would correspond to that if the flat-panel detector 14 had been positioned in its necessitated position. The correction data 28 may now contain different pieces of information. For example, the correction data 28 determine neighboring pixels 54 of the radiation penetration raw image for each pixel 56 of the radiation penetration image according to a specification which varies among the pixels of the radiation penetration image according to the geometrical correction, and how the same are to be combined with respect to the respective pixel 56 of the radiation penetration image. It is important to note here that the weighting of the pixels 54 in the resolution of the pixel grid 52 varies, i.e. in a higher resolution than the resolution of the final radiation penetration images. The correction data 28 could, for example, execute a new interpolation for each shifted position of the individual pixels 54 and then execute the binning. This is indicated by subdivision of the pixel 56 in FIG. 4. A different process is, however, also possible, according to which the flat or planar overlap of the respective pixels 54 with the pixel 58 shifted with respect to the geometrical correction is evaluated in order to acquire the weighting contribution for the final radiation penetration image.

As already mentioned, it is of advantage for the preprocessor 24 to directly receive the radiation penetration raw images in the form of pixel information of the pixels 48 in the distribution 42. The preprocessor 24 is in this case responsible for the complete correction measures, i.e. the above-mentioned stitching, the distortion correction and the position correction for the cameras 38₁ and 38₂ within the flat-panel detector 14 and the geometrical correction for the virtual position correction of the flat-panel detector 14 in the axes system 20 of the radiation penetration system 10. In the following, with reference to FIG. 2, a method for calibrating the radiation penetration system 10 of FIG. 1 is described for this case, i.e. for the case of a flat-panel detector 14 comprising an irregularity of the pixel distribution in the image plane, wherein the preprocessor 24 directly receives the radiation penetration raw images comprising this irregularity.

In the following description of a calibration method it is assumed that the flat-panel detector 14 comprises an irregularity in the distribution of pixel positions in the image plane or the projection plane of the flat-panel detector 14, as, for example, results from conditions explained with reference to FIGS. 3 and 4. In this case the method comprises, for example, in addition to steps 30 and 32, before the same the step of providing 60 the flat-panel detector 14 in a pre-calibrated state, wherein the correction data 28 are preset such that the same correct the irregularity of distribution of the pixel positions in the image plane, so that the application of the correction data 28 set as mentioned leads to the fact that the radiation penetration image comprises a regular pixel grid at the output of the preprocessor 24, such as, e.g., the pixel grid of the pixels 56, as has been indicated in FIG. 4. The imaging in step 30 is executed in this pre-calibrated state, possibly, however, without binning. This enables the following advantage: the device 34 does not use the pure raw images put together from the partial images 50, as indicated by the arrow 62 in FIG. 1, and which would, of course, also be possible, but the device 34 uses, for resetting or readjusting the correction data 28, the radiation penetration raw images gained in the one or the several radiation exposures in step 30 in a corrected form corrected by the preset correction data 28 with respect to the irregularity of distribution of the pixel positions in the image plane, as is indicated by the arrow 64 in FIG. 1. I.e., the calculation of the modification of the correction data 28 in step 32 by the device 34 is simplified, as it may be assumed in the calculation that the underlying information already exists in a regular pixel grid, such as, e.g., the pixel grid 52 of FIG. 4, or even the coarse pixel grid with the pixel 56. Upon step 32, the correction data 28 exist in a modified form which, for example, indicate for each shifted coarse pixel 28 of the radiation penetration images how the underlying original pixels 48 are to be combined in the image plane 38 using which weighting in order to result in the respective pixel 56. In subsequent radiation penetration measurements, the application of correction data 28 takes place only once, i.e. for the purpose of geometric correction of the position deviation of the flat-panel detector 14 in the axes system 20, the stitching of the partial images 50 and the distortion correction of these partial images, as has already been described above.

With reference to the description above, it is to be noted that although it is of advantage for the resolution of the radiation penetration raw images to be higher than the resolution of the radiation penetration images finally to be used, this is not necessary. According to further embodiments, this is not the case and the correction simply takes place in the resolution of all these images, i.e. in the resolution of the radiation penetration raw images and the radiation penetration images.

It is further to be noted with reference to the above-mentioned description that the radiation penetration system may, if applicable, additionally be implemented such that, for example, the source/detector distance is adjustable, such as, e.g., for acquiring different enlargements. If the pixel grid of the radiation penetration images finally to be used is equiangular, then additional corrections are necessitated after each adjustment of the distance, such as, e.g., between two measurements, when the distance is adjusted or changed. The correction data may then be determined, as illustrated in FIG. 2, such as, e.g., beforehand for different distances or anew every time after an adjustment of the distance. Real position errors of the detector would, if applicable, i.e. optionally, also be balanced here. Thus, FIG. 1 also describes a radiation penetration system with a radiation source 12 for generating radiation in a divergently; a flat-panel detector 14 for generating a radiation penetration raw image of an object 16 on the basis of the radiation 18 which penetrates the object 16 between the radiation source 12 and the flat-panel detector 14, wherein the radiation penetration system is constructed such that an axes system 20 is determined by the same and such that a distance between the radiation source and the flat-panel detector is adjustable; a preprocessor 24 for processing the radiation penetration raw image into an equiangular radiation penetration image, i.e. depending on the set distance. Readjustments of the mentioned distance would then be easily possible.

In the above description of FIG. 2, with respect to step 32, possibilities were not specifically mentioned as to how the correction data 28, which indirectly or directly include a determination of the position error, can be determined. In the following, for example with reference to FIGS. 7 and 8, a possibility is mentioned of determining a position error of the flat-panel detector 14 which normal to surface is tilted with respect to a state in which the flat-panel detector 14 would be in its necessitated position. As a measure for tilting, for example, two tilting angles are acquired which may then be converted into suitable geometric distortion parameters as the correction data. As was described above with reference to FIGS. 7 and 8, in this case a sphere of absorbing material can be used as a calibration object arranged eccentrically with respect to an axis of rotation of the manipulator 22, so that its center, in the projection onto the image plane of the flat-panel detector 14, describes a trajectory which is, for example, an ellipse, while the radiation source/flat-panel detector pair on the one hand or the sphere on the other hand are rotated around the axis of rotation. In particular, the trajectory of the sphere center in the projection forms a closed path which, depending on the tilting, is traversed faster in one half than in the other half of the same and, with no tilting, is traversed for example with a constant speed with respect to the angle of rotation or with a constant distance between the recordings generated with equidistant rotation angles of the manipulator. In other words, for example, the angle of rotation between recordings of the calibration object is changed with the same angular difference, and the resulting segment lengths between the corresponding center positions on the mentioned ellipse are evaluated in order to calculate the tilting angles. The use of a sphere as a calibration object, however, only represents one example of a calibration object for which a designated position—here the center—may be determined in the projection plane in step 32 in a relatively simple way, and particularly with sub-pixel accuracy, i.e., e.g., in a resolution which is, for example, even higher than the resolution of the original pixels 48. Other calibration objects may also have designated positions which are easy to determine, i.e. also more than one, such as, e.g., polyhedrons, like pyramids, cubes or the like. On the other hand, for example, a twisting or rotation of the flat-panel detector 14 with respect to its necessitated position around the surface normals of the projection plane of the flat-panel detector 14, i.e. the necessitated normal vector, for example with respect to a translation positioning axis of the manipulator 22, may be determined by positioning and recording a calibration object along this translation positioning axis at two different positions or several positions along this translation positioning axis. In this way, the angle between the line can easily be determined which the designated points of the calibration object take on in the projection plane with respect to the line and/or column direction, for example, of the pixel grid 52, in order to calculate the backwards rotation in this way. In a similar way, by the above-described tilting determination by the evaluation of the above-described position changes when the calibration object traverses the closed trajectory in the projection plane, the angle of the tilting axis, for example with respect to the column or line direction of the pixel grid 52 and the tilting angle around this tilting axis extending within the projection plane, may be determined, i.e. the angle of tilting around the tilting axis, which is again perpendicular to the desired normal vector. If a sphere is used as the calibration object as in the following examples, it is of advantage for the sphere, with respect to the original pixel grid 48 or the pixel grid 52, for example to take on an approximate size, so that the radius of the projection of this sphere into the projection plane of the flat-panel detector 14 takes more than three pixels, for example, so that by interpolation the position of the center can be determined with sub-pixel accuracy. The diameter may, for example, be 20 pixels.

In the following, further possible details are to be discussed which are also mentioned below with reference to FIGS. 5-12.

It is, for example, possible to enable the user of the radiation penetration system 10 to variably set the resolution of the radiation penetration images at the output of the preprocessor 24. The correction data 28 may be predetermined separately for each of these adjustment possibilities or be the same for all of these adjustment possibilities. For example, the adjustability of the resolution of the radiation penetration images at the output of the preprocessor 24 is restricted to a mere adjustability of the binning extent from the resolution in which the geometrical correction was executed to the resolution of the final radiation penetration images. For example, after the calibration, the correction data 28 are in a state in which they have modified weighting factors for each pixel 54—in the geometrically corrected position (within the big pixels 58)—which indicate how to combine the same from the original pixels 48, and the binning adjustment possibilities are restricted to an adjustment of the size of the n×n blocks, wherein the thus shifted counterparts of the pixels 54 are combined into coarse pixels 58. In FIG. 4, a 3×3 setting is illustrated, wherein, however, a 2×2 binning would also be possible. This binning which may be adjusted afterwards would thus be location-invariant across the image plane 36.

It is finally to be noted that it was frequently assumed above that the radiation penetration images exist at the output of the preprocessor 24 in a regular pixel grid which comprises columns and lines, for example in a Cartesian arrangement. This is, however, not absolutely necessary. It is to be noted in the following that it may be advantageous for different reasons or be requested by the reconstructor 26 that the pixel arrangements are subject to different regularities, such as, e.g., to be arranged in an equiangular manner in a column or line direction or in a radial direction and thus with a polar arrangement of the pixels. This is, however, not a fundamental problem. In this case, the correction data 28 indicate for one pixel from such a more general regular pixel arrangement, like for example the original pixel 48, how the pixels are to be combined with the respective target pixel in the radiation penetration image, i.e. with which weightings, to result in the respective target pixel of the radiation penetration images, wherein the geometrical correction is here contained in the weightings in a resolution which is greater than the final resolution of these radiation penetration images.

With respect to the embodiment of FIGS. 3 and 4 with the plurality of cameras $38_1$ and $38_2$, which practically act as a plurality of flat-panel detector arrays of the flat-panel detector 14, it is now to be noted once again that it may be the case that the correction data 28 in the overlap regions of the partial images 50 are set such that they define, for a pixel of the regular pixel grid of the radiation penetration images in an overlap region of the partial images 50, a combination of pixels which belong to two different neighboring partial images 50. That is even when this coarse pixel, such as, e.g., the pixel 58 in FIG. 4, only overlaps the overlap region or only a neighboring partial image 50 in the overlap region, but is otherwise completely contained within a partial image. In this way, the available image information is optimally utilized.

The above embodiments thus enable, using a camera which is not exactly aligned, but is, for example, exactly characterized with respect to the geometry, i.e. a pre-calibrated camera or a corresponding flat-panel detector 14, to generate images with pixel coordinates which are exactly aligned with respect to the overall system and more exactly to the axes system 20 of the same. It is to be noted that the above-described geometry corrections also discussed further below using concrete examples are not merely restricted to the calibration of X-ray cameras, but may also be used for any other applications wherein pixel data has to be generated in a certain recording geometry.

As was described above, it is possible, by a suitable geometrical data transformation operation in step 32, to gain a new image from the original pixel data, i.e. the pixel information at the pixels 48 of a camera which is not exactly aligned or a corresponding flat-panel detector 14, wherein the image fulfils requirements of the respective application with regard to the geometrical alignment, such as, e.g., the image with the pixels 56 in FIG. 4. Here, the new pixel values of the transformed image to be calculated are calculated from the pixel values of the original pixel data. In the simplest case, data to be calculated is calculated from the neighboring pixel values of the original image with the pixels 48 by means of a bilinear interpolation, i.e. not directly for the coarse pixels 56 but for all the pixels 54 in their shifted, geometrically corrected position. In the worst case, this causes the resolution of the image to be halved. Subsequently, binning may be executed as was described above.

The pre-calibration may, for example, be executed as described in patent DE 10 301 941, i.e. already with a higher resolution than the target resolution, wherein the resolution is not reduced to the desired measure until afterwards, i.e. by the mentioned binning. The corresponding correction data is then modified, as was described above with reference to FIG. 2 in the alternative comprising step 60. All in all, this causes the information loss by the geometrical correction to be clearly reduced or prevented. The geometrical image correction and combination of several pixel values may also be executed in one single processing step, as was described above, i.e. the binning and the geometrical correction for a position correction of the flat-panel detector 14.

Figure 11:
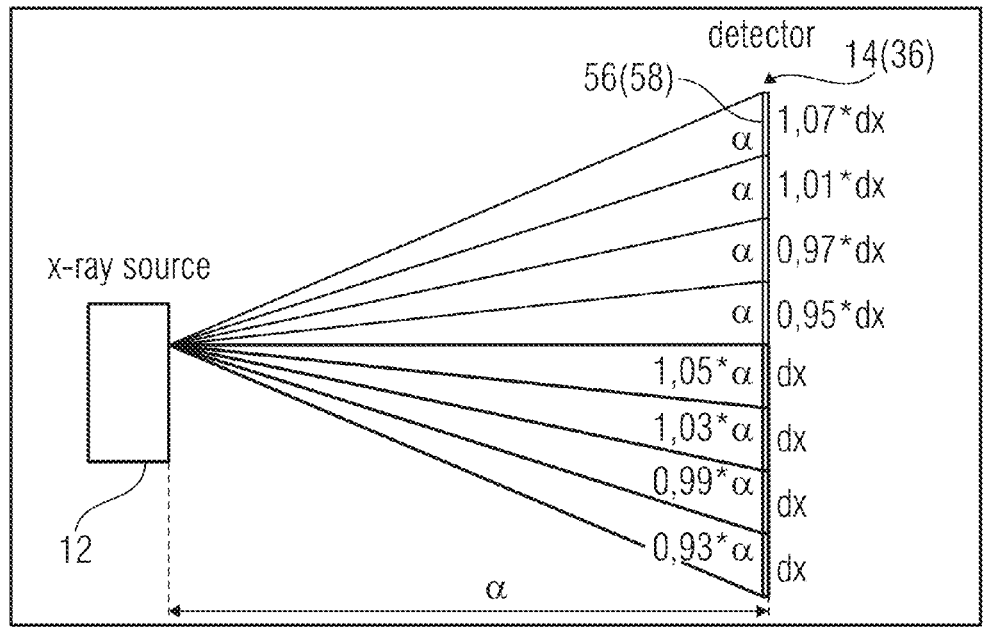
FIG. 11 is a schematical illustration of a radiation penetration system for illustrating a comparison between an equidistant and an equiangular pixel arrangement.

Within the scope of the geometrical adaptation of a recording in the above-mentioned way, which will be discussed again in the following, certain pixel arrangements may be generated which meet many different requirements and may deviate from a Cartesian pixel arrangement which could not be realized with detectors used up to now without a clear information loss:

1. Columns and lines are at a right angle with respect to each other. All pixels have a square shape and the same size. (standard radioscopy case)
2. The columns and lines of the image have a defined Cartesian orientation within an arrangement of an overall system (X-ray source, mechanical positioning axes). (standard CT case)
3. The pixels are not rectangular but have the same size, the pixel coordinates are not perpendicular to each other. (e.g. helical CT application)
4. The pixels have a rectangular shape with a different height and width. The ratio between height and width may take on any value.
5. The pixel extent and coordinates vary depending on the position on the detector.
6. Defined linear and non-linear image distortion, i.e. the orientation of the lines and/or columns depends on the position on the detector. By this, for example, a virtual spherical or cylindrical X-ray camera with an X-ray source point as a center point may be generated, wherein, for example, all pixels detect the same spatial angle or the same polar angle (OPED-CT). Further, using the method a real non-planar detector area may be converted into a virtual ideal-planar detector area. In the case of planar computed tomography (PCT), depending on the set irradiation angle the geometry correction may be operated such that also radiation penetration projections with a real non-planar detector area lead to correct reconstruction results. A further example of a realizable image transformation is to transform the recordings of an inclined detector such that the same correspond to the recordings of a perpendicular detector. The opposite case of transforming the recordings of a perpendicular detector so that they correspond to the recordings of a tilted or inclined detector is also possible. The effect of a re-transformation between a Cartesian (equidistant) and a virtually cylindrical (equiangular) X-ray camera is indicated in FIG. 11. FIG. 11 shows an example of a comparison between an equidistant (bottom) and an equiangular (top) pixel arrangement on an image or projection plane 36 of a detector 14. The bottom region of the detector 14 is divided into pixels of the same size dx. The top region of the detector is divided into pixels which cover the same angular range a. In the equidistant region, the covered angular range decreases to the outside. In the equiangular region of the detector, the pixel size increases to the outside.
7. Transformation of the pixel geometry, so that, e.g., all image points having the same distance to the center of the detector are imaged or mapped in one line. An increasing line index then corresponds to the growing distance to the center of the detector. The distance may, e.g., be determined as the distance on the detector or as an angle between the central beam and the beam onto the corresponding image point. The column index corresponds to the polar angle of the image point. The image described here may be referred to as unwrapping. (X-ray diffraction/diffractometry).

If the calibration or correction data 28, i.e. the calibration parameters describing the geometrical transformation of the pixel coordinates, are determined and stored for different situations, a radiation penetration system may be reconfigured with little effort by loading the corresponding parameters into a software or hardware component.

Describing the above embodiments again with reference to concrete cases of application and in other words, by a suitable process it may be determined how an original recording uncorrected with respect to position has to be transformed by a flat-panel detector 14 so that it meets the requirements of the overall imaging system or the radiation penetration system. This determination is executed in step 32 of FIG. 2. It may, for example, be determined by recordings of a known object in different known positions or orientations in which way the actual and the desired state of the recording differ, i.e. the actual position of the flat-panel detector 14 is different from its necessitated or desired position. The shape of the reference object and the way of recording depends on the type of calibration task. Using the information gained from the recordings, the mathematical form of the correction operation to be executed may be determined in step 32. The transformation of the image data, i.e. the application of the correction data 28 may, as mentioned above, be executed in a special part of the camera or the flat-panel detector 14 or in a location between the camera 14 and the data recording calculator or constructor 26 or directly within the latter. Following this geometrical transformation, then, according to one embodiment, a combination of neighboring pixels into the desired final pixel size 56 (binning) may be executed. If the geometry of the overall system changes due to a changed position of the flat-panel detector 14 or another component of the assembly 10, by loading adapted calibration data 28 of the detector 14 the latter may be adapted to the new situation.

Figure 7:
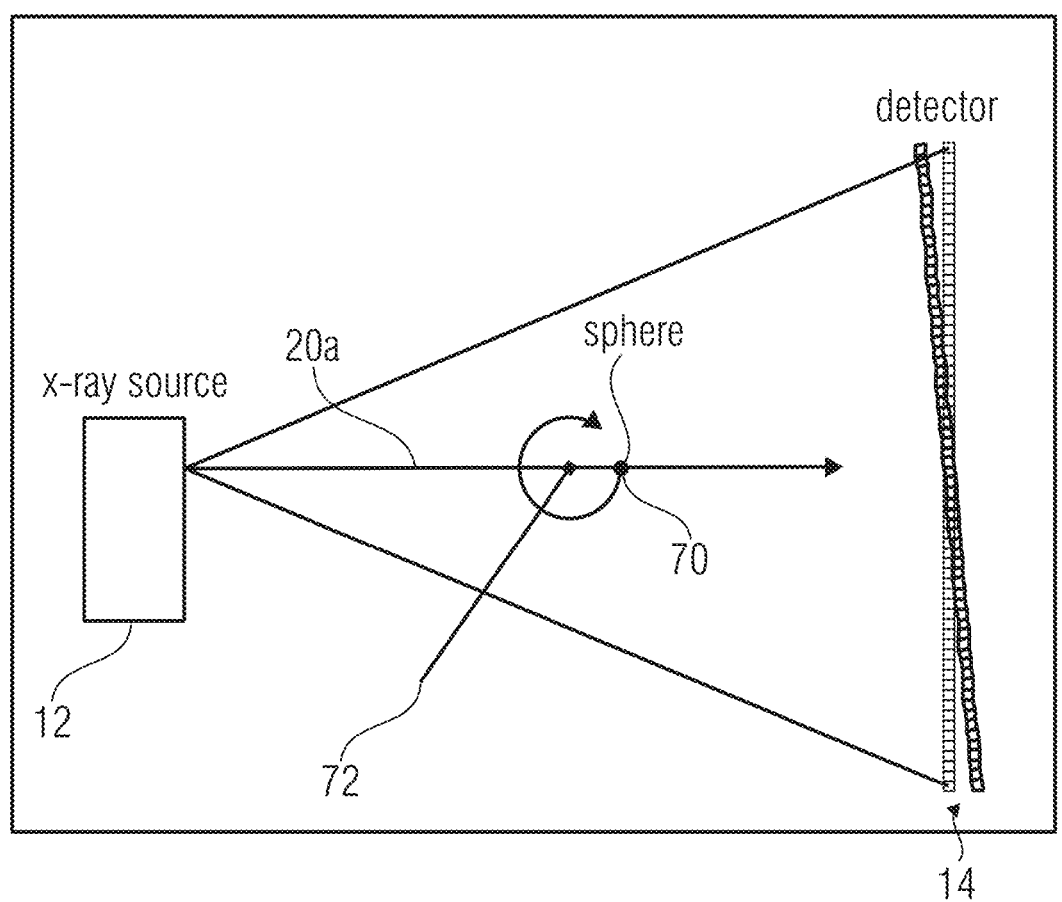
FIG. 7 is a schematical illustration for presenting one possible configuration for generating radiation penetration raw images for the calibration of a radiation penetration system according to one embodiment.

For the X-ray computer tomography (CT) the flat-panel detector 14 has to be exactly aligned, for example with respect to the mechanical axes system as specified by the manipulator 22, and should not change its position or orientation during data recording in order to prevent artifacts in the subsequent reconstruction of the recorded object in the reconstructor 26. In other words, the radiation penetration system 10 of FIG. 1 may, for example, be a computer tomograph, wherein it is the object of the installation of the system for the columns of the flat-panel detector 14 to be aligned in parallel to the axis of rotation of the manipulator 22, which is, for example, an object manipulator, i.e. a manipulator which moves the object relative to the radiation source 12 and the flat-panel detector 14. As was described above, it would, on the other hand, also be possible to leave the object in a fixed position. A possible tilting of the detector into the beam direction 20*a* and perpendicular to the same should actually be prevented in the installation as far as possible. This for example applies to all configurations of the beam source or the X-ray source 12, the manipulator 22 and the flat-panel detector 14. This results, with increasing stipulated detail resolution of the system 10, in increasing requirements on the geometrical accuracy of all mechanical components, such as, e.g., the linear and rotation axis of the system 10. A CT system according to FIG. 1 facilitates the effort with respect to mechanical adjustment, which would otherwise be necessitated in order to adjust the orientation of the mechanical axes and the detector. In order to illustrate this, in the following the method according to FIG. 2 for determining the correction data 28 for the CT example is presented in more detail. Reference is made to FIG. 7. An object 70 suitable for determining the correction data 28 is mounted relative to the axis of rotation or on the axis of rotation 72, around which the manipulator 22 rotates the pair consisting of the X-ray source 12 and the flat-panel detector 14 or the object 70.

Figure 8:
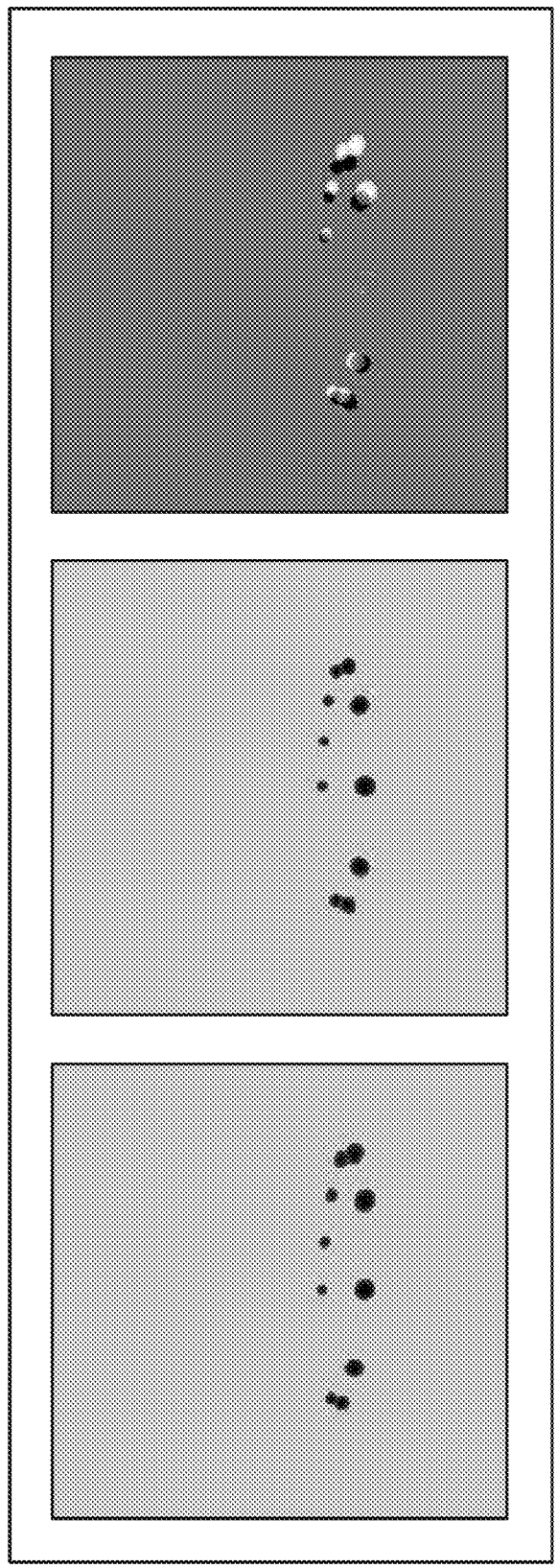
FIG. 8 shows simulated sequences of radiation penetration raw images with a sphere as a calibration object in a radiation penetration system according to FIG. 7, i.e. on the left with a tilted detector, in the center with an ideally adjusted detector and on the right the difference between the two images.

A suitable object 70 is, for example, a sphere of strongly absorbing material in a weakly absorbing material or a different object having characteristic structures whose positions can be determined in radiation penetration recordings. In FIG. 8, in the configuration of the CT assembly according to FIG. 7, three sequences of a sphere for different recording geometries are illustrated, i.e. for different angles of rotation around the axis of rotation 72, all drawn into one image, i.e. on the left for a non-adjusted or tilted camera 14*b*, in the center for an adjusted camera 14*a*, and on the right the difference between both images. The object 70 is thus recorded in different angular positions around the axis of rotation 72 (step 30). Each point of the reference object 70, i.e. the center point of the sphere, here describes a circular path. The projection of this circular path onto the image plane of the flat-panel detector 14 results in an ellipse. From the deviation between the measured paths of the reference points and those for an adjusted detector in the projection plane, the geometrical transformation may be determined in step 32.

If the flat-panel detector 14 is tilted around the beam direction 20*a*, the raw image, such as, for example, the pre-calibrated image with the pixel grid 52 or the raw image of the pixel 48, is directly rotated in the preprocessor 24 by a defined angle before the thus acquired pixels, i.e. the smaller pixels which are combined into pixel 56 in FIG. 4, are combined into the desired resolution (binning). If the detector is tilted around the column and/or the line direction of the pixels, such as, e.g., pixels 54, the necessitated image correction corresponds to a distortion, as may be gathered from FIGS. 5 and 6, which is, for example, executed before binning, as mentioned. By such an image correction it becomes possible to partially omit especially precise and complex mechanical components of the assembly and replace the same by less precise and complex ones, as the assembly 10 may be adapted to any situation by calibration. Only the axis of rotation 72 for the object 70 has to further meet the requirements by the desired resolution and accordingly have the least possible stagger.

Figure 5:
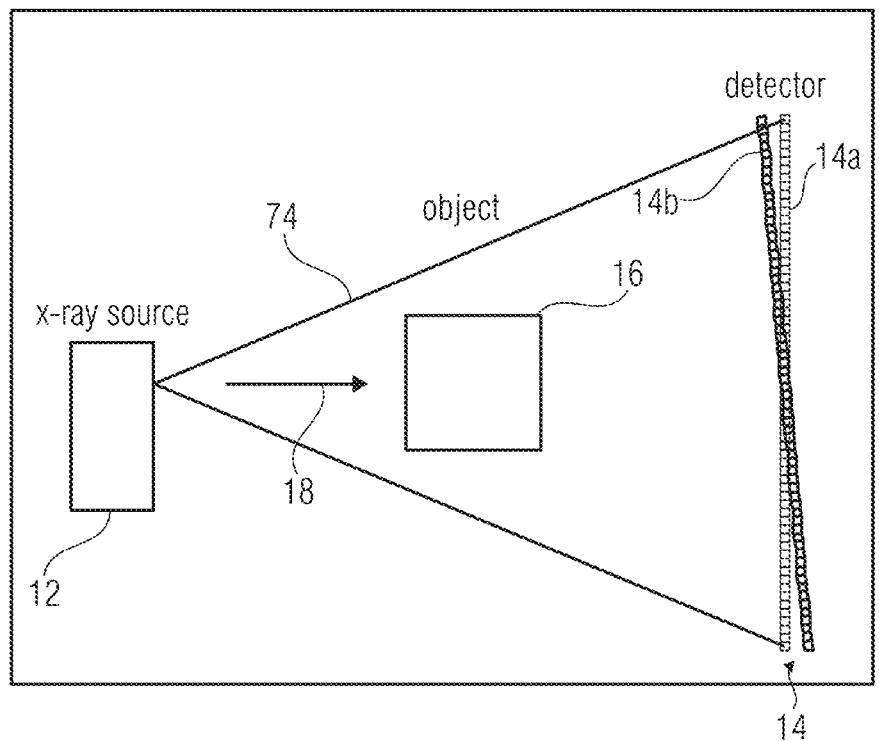
FIG. 5 is a schematical sectional side view for illustrating an example of a position error of the flat-panel detector.

Again describing FIGS. 5 to 8 in other words, these figures show an X-ray assembly as an example of a radiation penetration system by means of a schematic diagram. In FIGS. 5 and 7 the X-ray source 12 with the divergent radiation cone 74 of the radiation 18 is illustrated. The detector 14 is illustrated in FIGS. 5 and 7 in two different orientations, one time 14*a* in the necessitated position or the ideal orientation, and the other time 14*b* with a position error, which here is exemplarily a lateral tilting with respect to the beam axis 20*a*. A cube has been exemplarily selected as the object 16. FIG. 6 shows the simulation of radiation penetration recordings of a cube in the two positions 14*a* (right) and 14*b* (left). The simulations thus correspond to the two detector orientations 14*a* and 14*b* in FIG. 5 or 7. On the left, thus a lateral tilting of the flat-panel detector 14 has been simulated, whereas on the right the recording is illustrated with an adjusted (not tilted) flat-panel detector 14. The arrows 76 connect corresponding points in the projections of the cube 16.

FIG. 7 now illustrates one possible arrangement for the calibration of the flat-panel detector 14 of FIG. 5 which is completely out of adjustment. Here, a sequence of recordings of a sphere as the calibration object 70 is generated. For each individual recording, the sphere 70 is moved on by a defined angle around the axis of rotation 72. Simulations of such sequences are illustrated in FIG. 8. In particular, FIG. 8 shows simulated sequences of X-ray recordings of the sphere 70 in the recording geometry, as it is illustrated in FIG. 7. It has been simulated in the left-hand partial image what the sequence looks like when the flat-panel detector 14 is in position 14*b*, i.e. laterally tilted. The central image shows the result with an ideal adjustment of the flat-panel detector 14, i.e. in position 14*a*. On the right, the difference between the tilted and the adjusted recording is illustrated. This difference, if it is not corrected, would cause an error in a subsequent use of the radiation penetration images in the reconstructor 26, and in a form which, although it has been corrected, is corrected only in the final resolution, part of the error would still remain in the recordings. According to the above embodiments, this is prevented by executing the correction in a higher resolution.

Subsequently, now the advantages of the inventive method for the planar tomography (PCT) are to be illustrated. With planar tomography, according to standard up to now, with an approximately planar object with a constant orientation, the X-ray source and the X-ray camera are sequentially positioned with respect to the object in parallel planes, wherein the axial planes are aligned in parallel to the main plane of the object. The plane of the active area of the X-ray camera is also aligned in parallel to the other planes. In other words, for example, the system of FIG. 1 represents a system for planar tomography and a manipulator 22 exits which comprises translation positioning axes which together form a plane, with respect to which the radiation source/flat-panel detector pair, on the one hand, and the object, such as, e.g., a circuit board, on the other hand, are moved translationally with respect to each other. The assembly is used, for example, to detect solder points of bad quality. In the necessitated position, the projection plane of the flat-panel detector 14 is plane-parallel to the positioning plane of the manipulator 22. Once this alignment has been executed, the object reconstruction may take place from the processing of several projection recordings from different directions. A possibly existing deviation of the active surface of the X-ray camera from the ideal plane generally leads to errors, so-called artifacts, in object reconstruction. The deviation of the projection plane of the flat-panel detector 14 from the ideal plane may have different reasons, such as, e.g., one of the previously mentioned reasons, such as, e.g., tilting with respect to the beam axis, twisting with respect to the beam axis or the manipulator positioning axis or the like. There may further be a distortion possibly resulting from the fact that the projection plane of the flat-panel detector 14, such as, e.g., the screen 36 of the scintillator, has a certain curvature which deviates from an ideal planar shape. The latter deviation possibility of course also applies to all the other embodiments. Any such deviations from the ideal plane may be corrected according to the described embodiments by suitable calibration. This is to be described again specifically for the case of application of planar tomography.

As an object for determining the correction data 28, either a flat plate of strongly absorbing material having defined holes or a flat plate of slightly absorbing material having structures of strongly absorbing material may be used. The holes or structures serve as reference points which may be detected in step 32 or whose positions may be determined in the image plane in step 32, just as was the case in FIG. 7 above. Instead of the object to be examined, such as, e.g., circuit boards, the plate (board) has to be positioned in the assembly such that it is parallel to the planes of the detector and tube movement. If the detector or tube or object are linearly positioned or moved by a defined distance, the positions of the reference points found in the projections of the object on the detector with a regular arrangement of square pixels describe, in the ideal case, straight lines. If the direction of movement corresponds to the desired alignment of the detector lines or columns, the necessitated parameters for correction of an incorrect adjustment may be determined from the deviation of the change of position of the projected reference points with respect to a pixel line or column. If the detector or tube or object are again moved by the same distance, the projection of a reference point is, in the ideal case, again shifted by the same distance as in the first step. For example, between the recordings of the calibration object, the recording constellation is changed by the manipulator such that with an ideal position and alignment of the detector in the projection plane a position of the designated point of the calibration object in the projection plane would result, which would be located on a square, i.e., for example, in parallel to the columns and lines of the detector. Different procedures would, of course, also be possible. This takes place in step 30. If the length and/or the direction of shifting the projection changes, the plane of the scintillator screen 36 is not parallel to the plane which is spanned by the positioning axes and/or the scintillator screen 36 is not ideally planar. From the deviations of the reference point positions on the detector for different tube or detector or object positions, the geometrical correction of the image data may be determined in step 32 so that they meet the requirements for planar tomography. In particular, a calibration object with a sufficiently dense arrangement of reference points may serve to determine the tilting or arching of the scintillator screen 36 without moving a component of the assembly. If the reference points are arranged, e.g., equidistantly, also the projections of the reference points are ideally to be arranged equidistantly. The camera image may be adjusted by rotation and, if applicable, equalization before pixel binning with respect to the axes system in the preprocessor. Further, in the described way, the correction of image distortion due to an arched scintillator surface with inclined irradiation is possible by including a-priori information on the irradiation angle. If applicable, a correction of the arched scintillator is to be determined and applied for each detector position or beam direction.

A further embodiment of the radiation penetration system of FIG. 1 is the implementation in the form of a spiral CT assembly. With the spiral CT the object or detector 14 and the X-ray tube as the radiation source 12 are displayed synchronous to the rotation of the object 16 in the direction of the axis of rotation. For the reconstruction, the individual projections have to be filtered in a diagonal direction. The angle of the filtering direction again depends on the ratio between the rotation and feed speed. To be able to perform filtering, each recording is mathematically transformed such that the lines are aligned in parallel to the filtering direction. According to the above embodiments, the occurrence of information loss is now prevented, as the transformation is already executed with the high-resolution raw data, so that the information loss by the necessitated rotation is minimized.

For a certain CT reconstruction algorithm (OPED; orthogonal polynomial expansions on the disk), projection recordings are necessitated whose pixels are arranged in an equiangular manner with respect to the X-ray source. A circularly bent detector having its circle center in the focal spot of the X-ray source, whose pixels all have the same size, would meet this requirement exactly for a certain distance (or radius) between the detector and the X-ray source. Different distances between the X-ray source and the detector could not be realized here. A planar detector whose pixels become continuously wider towards the edge according to the condition of constant angular distances may fulfill this condition, as is indicated in FIG. 11 in the upper half of the detector 14. As the pixel size is variably adjustable using the method described here, an equiangular pixel format may be generated for all possible detector-source distances, i.e. as is illustrated in the upper half in FIG. 11. The exact necessitated pixel format may be calculated from knowing the detector-source distance d or be determined using calibration recordings and adapted to the requirements of a certain check task.

In powder diffractometry, ring-shaped diffraction patterns result on a flat detector. The recording may be transformed geometrically such that the radial gray-scale course for fixed polar angles is illustrated, for example, along the columns of the output image. Accordingly, then the gray-scale course for a fixed distance to the center and the variable polar angle is illustrated in one line. The data for structural analysis may be gained more easily from this illustration.

For some years, X-ray cameras have been used which utilize the optical imaging of an X-ray-sensitive scintillator screen onto an optically sensitive image sensor by means of lens optics. Generally, such images generated by lens optics are distorted. In this case, a geometrical correction of a recording is mandatory in order to acquire an undistorted image. If the necessitated distortion correction is combined with one of the above-described geometrical transformations for geometry calibration in one single transformation step, no further information thus results.

Figure 9:
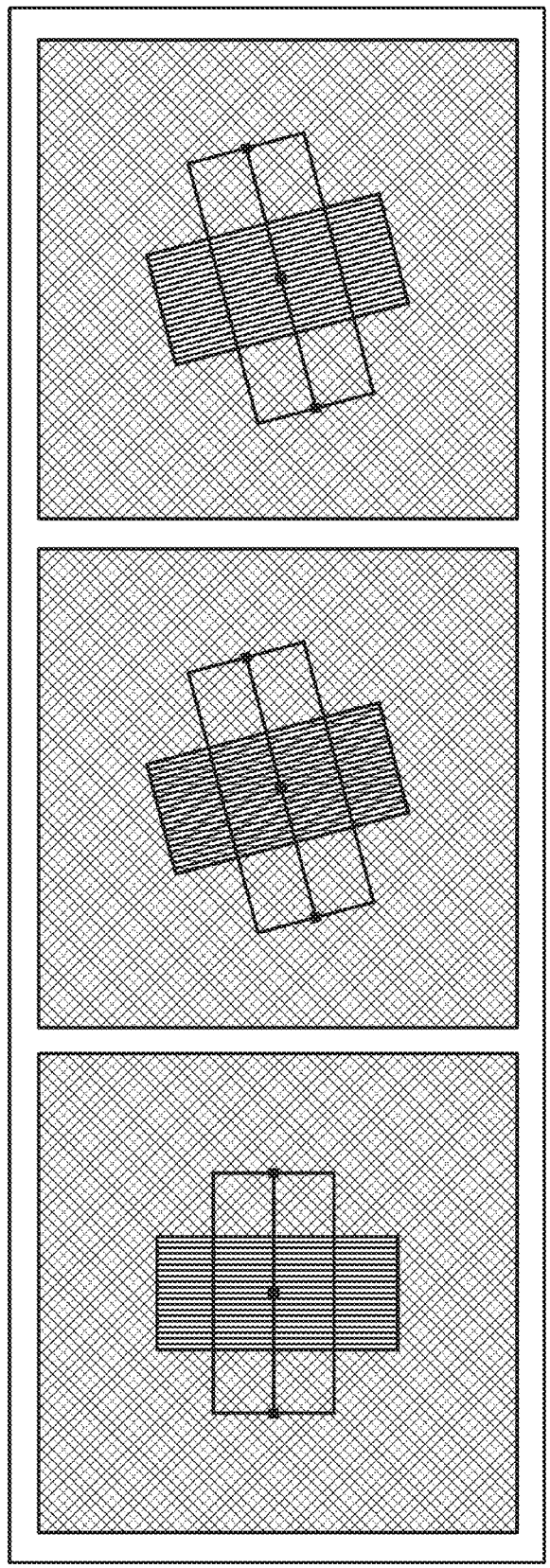
FIG. 9 shows simulated radiation penetration raw images of a line grating for illustrating the resolution loss by geometric transformation which is carried out in the resolution of the radiation penetration images.
Figure 10:
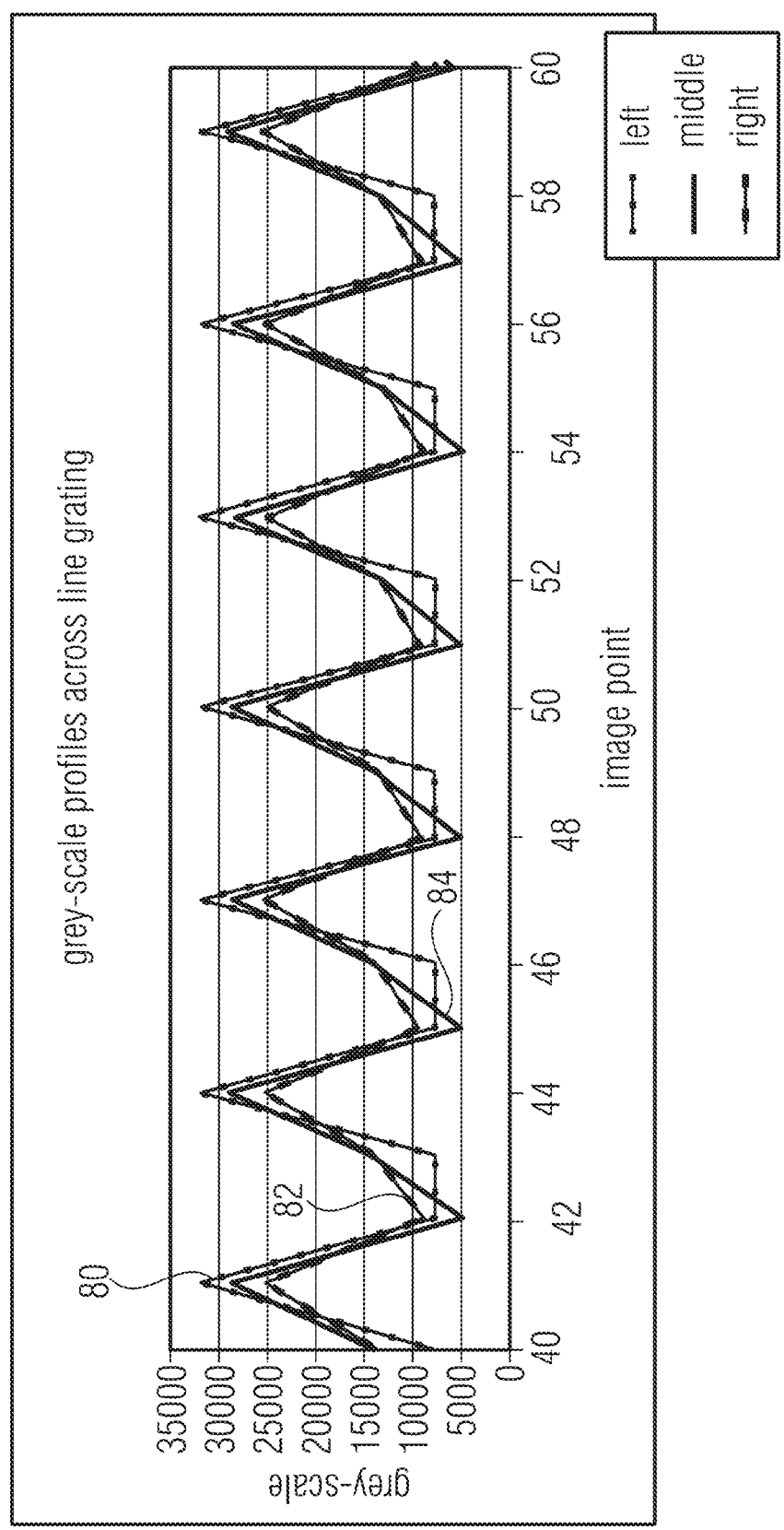
FIG. 10 shows grayscale profiles across the line grating of FIG. 9.

Finally, FIG. 9 shows simulated recordings of a line grating, recorded, for example, using a configuration according to FIG. 5. The simulations were generated for the demonstration of the resolution loss by geometrical transformation with a coarse resolution. On the left, the recording of a line grating is illustrated, whose column width and column distances are 1.5 image points. The center image shows the left recording after a rotation of the image around a defined angle. For the right-hand image, the recording was simulated with 4-fold resolution and then rotated around the same angle. Afterwards, the resolution was reduced to a quarter. Along the red lines, grayscale profiles were generated, which are illustrated in FIG. 10. The profile 80 illustrates the brightness course across the left and the profile 82 across the center line grating of FIG. 9. It may be clearly seen that, by the rotation of the recording, contrast is lost. The profile 84 represents the brightness course across the right grating. If the rotation of the recording is executed with a higher resolution, the form of the profile changes, but the contrast is essentially maintained. FIGS. 9 and 10 illustrate that the above-mentioned execution of geometrical correction with a resolution which is higher than the final resolution of the radiation penetration images, such as, e.g., directly at the untreated raw images of the flat-panel detector 14, has advantages with respect to the quality of the acquired radiation penetration images or recordings.

Figure 12:
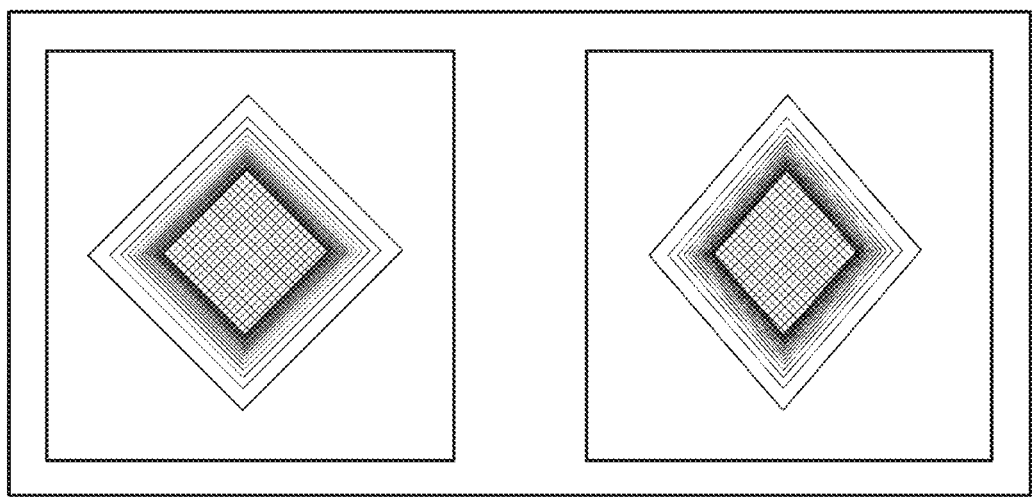
FIG. 12 shows simulations of radiation penetration images, one time with a detector having square pixels and the other time with a varying pixel width.

FIG. 12 finally shows simulations of the radiation penetration recording of a cube rotated by 45° around the beam direction. On the left, the recording of the cube with a detector 14 is illustrated whose pixels are square. On the right, a recording of the same cube is illustrated wherein the pixel width varies such that the pixels, with respect to the focal spot of the X-ray source, have the same angular width (see FIG. 11). Here, the recording seems to be more compressed towards the outside as the real pixel size increases (see also FIG. 11).

Although some aspects were described in connection with a device, it is obvious that these aspects also represent a description of the corresponding method, so that a block or a member of a device is also to be regarded as a corresponding method step or as a feature of a method step. Analogously to this, aspects which were described in connection with or as a method step also represent a description of a corresponding block or detail or feature of a corresponding device. Some or all of the method steps may be implemented by a hardware apparatus (or using a hardware apparatus), such as, e.g., a microprocessor, a programmable computer or an electronic circuit. In some embodiments, some or several of the most important method steps may be executed by such an apparatus.

Depending on certain implementation requirements, embodiments of the invention may be implemented in hardware or in software. The implementation may be executed using a digital storage medium, for example a floppy disc, a DVD, a Blu-ray disc, a CD, an ROM, a PROM, an EPROM, an EEPROM or a FLASH memory, a hard disc or another magnetic or optical memory on which electronically readable control signals are stored which may cooperate or do cooperate with a programmable computer system such that the respective method is executed. Thus, the digital storage medium may be computer-readable.

Some embodiments according to the invention thus include a data carrier comprising electronically readable control signals which are able to cooperate with a programmable computer system such that one of the methods described herein is executed.

In general, embodiments of the present invention may be implemented as a computer program product having a program code, wherein the program code is operative to execute one of the methods when the computer program product is executed on a computer.

The program code may, for example, be stored on a machine-readable carrier.

Other embodiments include the computer program for executing one of the methods described herein, wherein the computer program is stored on a machine-readable carrier.

In other words, one embodiment of the inventive method is thus a computer program comprising a program code for executing one of the methods described herein when the computer program is executed on a computer.

A further embodiment of the inventive method is thus a data carrier (or a digital storage medium or a computer-readable medium) on which the computer program for executing one of the methods described herein is recorded.

A further embodiment of the inventive method is thus a data stream or a sequence of signals representing the computer program for executing one of the methods described herein. The data stream or the sequence of signals may, for example, be configured in ordered to be transferred via a data communication connection, for example via the internet.

A further embodiment includes a processing means, for example a computer or a programmable logic device configured or adapted to execute one of the methods described herein.

A further embodiment includes a computer on which the computer program for executing one of the methods described herein is installed.

A further embodiment according to the invention includes a device or a system which is implemented to transfer a computer program for executing at least one of the methods described herein to a receiver. The transfer may be carried out electronically or optically. The receiver may be, for example, a computer, a mobile device, a memory device or a similar device. The device or the system may include, for example, a file server for transferring the computer program to the receiver.

With some embodiments, a programmable logic device (for example a field-programmable gate array, an FPGA) may be used to execute some or all functionalities of the methods described herein. In some embodiments, a field-programmable gate array may cooperate with a microprocessor to execute one of the methods described herein. In general, the methods are executed in some embodiments by any hardware device. The same may be a universally usable hardware, such as a computer processor (CPU), or hardware which is specific for the method, such as an ASIC, for example.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A method for calibrating a radiation penetration system comprising a radiation source, a flat-panel detector for generating radiation penetration raw images of an object, a manipulator which is implemented to change a relative position between the radiation source, the object and the flat-panel detector, wherein the axes system is defined by at least one movement axis of the manipulator and one beam axis between the radiation source and the flat-panel detector, and a preprocessor for applying correction data to the radiation penetration raw images of the object to acquire radiation penetration images of the object, comprising generating radiation penetration raw images of a calibration object in different relative positions changed with respect to each other by the manipulator between the radiation source, the calibration object and the flat-panel detector on the basis of radiation which penetrates the calibration object between the radiation source and the flat-panel detector, by the flat-panel detector; and readjusting the correction data depending on the radiation penetration raw images of the calibration object so that the application of the readjusted correction data leads to a geometrical correction of the radiation penetration raw images, so that a change of a projection of the object in the radiation penetration raw image due to a position error of the flat-panel detector in the axes system relative to a necessitated position is reduced, wherein the position error of the flat-panel detector is defined as a tilting of a column or line direction of the flat-panel detector relative to a rotation or translation positioning axis of the manipulator, or a tilting of the column or line direction of the flat-panel detector relative to a trajectory along which the flat-panel detector moves relative to the object between the plurality of radiation penetration raw images, wherein the preprocessor is implemented such that the same applies the correction data to the radiation penetration raw images of the object so that radiation penetration images of the object acquired therefrom comprise a lower resolution than the radiation penetration raw images of the object and that the readjustment of the correction data is executed depending on the radiation penetration raw images of the calibration object such that the geometrical correction takes place in a resolution which is higher than the resolution of the radiation penetration images of the object.

2. The method according to claim 1, wherein the flat-panel detector comprises an irregularity in the distribution of pixel positions in an image plane of the flat-panel detector and the method further comprises providing the flat-panel detector in a pre-calibrated state, wherein the correction data is preset such that the same correct the irregularity of distribution of the pixel positions in the image plane, so that the application of the thus preset correction data leads to a regular pixel grid, wherein the generation is executed in the pre-calibrated state and the readjustment uses the radiation penetration raw images of the calibration object in a version wherein the preset correction data are applied to the same.

3. The method according to claim 1, wherein the radiation penetration system further comprises a reconstructor which is implemented to reconstruct the object from a plurality of radiation penetration images which were acquired by the processor from radiation penetration raw images which were generated by the flat-panel detector by changing the relative position between the radiation source, the object and the flat-panel detector between the radiation penetration raw images, wherein the reconstructor is implemented to assume a position correctness of the flat-panel detector in the axes system in the reconstruction.

4. The method according to claim 1, wherein the readjustment is executed such that the newly adjusted correction data determine, for each pixel of the radiation penetration images of the object according to a specification which varies from pixel to pixel of the radiation penetration image according to the geometrical correction, which and how neighboring pixels of the radiation penetration raw images of the object are to be combined with respect to the respective pixel.

5. The method according to claim 3, wherein the preprocessor and the reconstructor are implemented such that the resolution of the radiation penetration images of the object is adjustable by adjusting a binning extent from the resolution in which the geometrical correction is executed to the resolution of the radiation penetration images of the object.

6. The method according to claim 1, wherein the readjustment is executed such that the readjusted correction data determine, for each pixel of a regular pixel grid with an intermediate resolution which is equal to or smaller than the resolution of the radiation penetration raw images of the object and higher than or equal to the resolution of the radiation penetration images of the object, a combination of pixels of the radiation penetration raw images of the object which comprise pixels of the radiation penetration raw images of the object which overlap the respective pixel of the regular pixel grid by less than 100% in area.

7. The method according to claim 6, wherein the intermediate resolution is higher than the resolution of the radiation penetration images of the object.

8. The method according to claim 6, wherein the flat-panel detector comprises a plurality of flat-panel detector arrays for generating partial images which, by mutually overlapping, together result in the radiation penetration raw images of the object, wherein the readjustment is executed such that the readjusted correction data determine one pixel of the regular pixel grid as a combination of pixels of two neighboring partial images.

9. A radiation penetration system comprising:
a device for calibrating the radiation penetration system,
a radiation source,
a flat-panel detector for generating radiation penetration raw images of an object,
a manipulator which is implemented to change a relative position between the radiation source, the object and the flat-panel detector, wherein the axes system is defined by at least one movement axis of the manipulator and a beam axis between the radiation source and the flat-panel detector, and
a preprocessor for applying correction data to the radiation penetration raw images of the object to acquire radiation penetration images of the object,
the device for calibrating the radiation penetration system comprising
a generator for generating radiation penetration raw images of a calibration object in different relative positions changed with respect to each other by the manipulator between the radiation source, the calibration object and the flat-panel detector on the basis of radiation which penetrates the calibration object between the radiation source and the flat-panel detector, by the flat-panel detector; and a readjuster for readjusting the correction data depending on the radiation penetration raw images of the calibration object so that the application of the readjusted correction data leads to a geometrical correction of the radiation penetration raw images, so that a change of a projection of the object in the radiation penetration raw image due to a position error of the flat-panel detector in the axes system relative to a necessitated position is reduced, wherein the position error of the flat-panel detector is defined as a tilting of a column or line direction of the flat-panel detector relative to a rotation or translation positioning axis of the manipulator, or a tilting of the column or line direction of the flat-panel detector relative to a trajectory along which the flat-panel detector moves relative to the object between the plurality of radiation penetration raw images, wherein the preprocessor is implemented such that the same applies the correction data to the radiation penetration raw images of the object such that the radiation penetration images of the object acquired therefrom comprise a lower resolution than the radiation penetration raw images of the object, and the readjuster for readjusting is implemented to execute the readjustment of the correction data depending on the radiation penetration raw images of the calibration object, so that the application of the readjusted correction data leads to a geometrical correction of the radiation penetration raw images of the object, so that the geometrical correction takes place in a resolution which is higher than the resolution of the radiation penetration images of the object.

10. The radiation penetration system according to claim 9, wherein the flat-panel detector comprises an irregularity in the distribution of pixel positions in an image plane of the flat-panel detector and wherein the flat-panel detector is in a pre-calibrated state, wherein the correction data is preset such that the same correct the irregularity of distribution of the pixel positions in the image plane, so that the application of the thus preset correction data leads to a regular pixel grid, the generator for generating executes the generation in the pre-calibrated state and the readjuster for readjusting uses the radiation penetration raw images of the calibration object in the readjustment in a version wherein the preset correction data are applied to the same.

11. The radiation penetration system according to claim 9, wherein the radiation penetration system further comprises a reconstructor which is implemented to reconstruct the object from a plurality of radiation penetration images which were acquired by the processor from radiation penetration raw images which were generated by the flat-panel detector by changing the relative position between the radiation source, the object and the flat-panel detector between the radiation penetration raw images, wherein the reconstructor is implemented to assume a position correctness of the flat-panel detector in the axes system in the reconstruction.

12. The radiation penetration system according to claim 9, wherein the readjuster for readjusting is implemented to execute the readjustment such that the readjusted correction data determine, for each pixel of the radiation penetration images of the object, according to a specification which varies from pixel to pixel of the radiation penetration image in accordance with the geometric correction, which and how neighboring pixels of the radiation penetration raw images of the object are to be combined to the respective pixel, i.e. using a weighting of the pixels of the radiation penetration raw images of the object, which depends on the resolution in which the geometrical correction is executed.

13. The radiation penetration system according to claim 11, wherein the preprocessor and the reconstructor are implemented such that the resolution of the radiation penetration images of the object is adjustable by adjusting a binning extent from the resolution in which the geometrical correction is executed to the resolution of the radiation penetration images of the object.

14. The radiation penetration system according to claim 9, wherein the readjuster for readjusting is implemented to execute the readjustment such that the readjusted correction data determine, for each pixel of a regular pixel grid with an intermediate resolution which is equal to or smaller than the resolution of the radiation penetration raw images of the object and higher than or equal to the resolution of the radiation penetration images of the object, a combination of pixels of the radiation penetration raw images of the object which comprise pixels of the radiation penetration raw images of the object which overlap the respective pixel of the regular pixel grid by less than 100% in area.

15. The radiation penetration system according to claim 14, wherein the intermediate resolution is higher than the resolution of the radiation penetration images of the object.

16. The radiation penetration system according to claim 14, wherein the flat-panel detector comprises a plurality of flat-panel detector arrays for generating partial images which, by mutually overlapping, together result in the radiation penetration raw images of the object, wherein the readjuster for readjusting is implemented to execute readjustment such that the readjusted correction data determine one pixel of the regular pixel grid as a combination of pixels of two neighboring partial images.

17. The radiation penetration system according to claim 14, wherein a location-invariant binning of the intermediate resolution leads to the resolution of the radiation penetration images of the object.

18. The radiation penetration system according to claim 9, wherein the calibration object is a sphere, a polyhedron, a flat plate with holes or a flat plate of less absorbing material comprising structures of more strongly absorbing material.

19. The radiation penetration system according to claim 9, wherein the readjuster for readjusting is implemented to determine a designated point of the calibration object for the different relative positions between the radiation source, the calibration object and the flat-panel detector in the radiation penetration raw images of the calibration object and to execute the readjustment depending on the designated point for the different relative positions.

20. The radiation penetration system according to claim 19, wherein the readjuster for readjusting is implemented such that the different relative positions are acquired by a rotation of the radiation source and the flat-panel detector or the calibration object by the manipulator around the axis of rotation of the manipulator.

21. The radiation penetration system according to claim 20, wherein the readjuster for readjusting is implemented such that an angle of rotation between the radiation penetration raw images of the calibration object comprising the same angular difference changes, and is implemented to evaluate resulting segment lengths between the designated point for the changing angle of rotation on an ellipse which the same describes for changing angles of rotation on the image plane of the flat-panel detector in order to calculate a tilting angle of the tilting of the image plane of the flat-panel detector.

22. The radiation penetration system according to claim 19, wherein the readjuster for readjusting is implemented such that the different relative positions are acquired by rectilinearly moving the radiation source, the flat-panel detector or the calibration object by the manipulator, by the calibration object being a flat plate with holes or a flat plate of less absorbing material comprising structures of more strongly absorbing material which is parallel to translation positioning axes of the manipulator, and the readjuster for readjusting is implemented to execute the readjustment depending on a deviation of a change of position of the designated point with respect to a pixel line or a pixel column of the flat-panel detector.

23. The radiation penetration system according to claim 9, wherein the readjuster for readjusting the correction data is implemented such that the position error of the flat-panel detector additionally comprises tilting of an image plane of the flat-panel detector from a perpendicular alignment with respect to a beam axis between the radiation source and the flat-panel detector.

24. A non-transitory computer-readable medium having stored thereon a computer program comprising a program code for executing the method according to claim 1 when the program is executed on a computer.

\* \* \* \* \*